US012290271B2

(12) United States Patent
Nevins et al.

(10) Patent No.: US 12,290,271 B2
(45) Date of Patent: May 6, 2025

(54) SYSTEM AND METHOD FOR LOCATION DETERMINATION USING MOVEMENT BETWEEN OPTICAL LABELS AND A 3D SPATIAL MAPPING CAMERA

(71) Applicants: Russell Todd Nevins, Las Vegas, NV (US); David Jon Backstein, Toronto (CA); Bradley H. Nathan, Toronto (CA)

(72) Inventors: Russell Todd Nevins, Las Vegas, NV (US); David Jon Backstein, Toronto (CA); Bradley H. Nathan, Toronto (CA)

(73) Assignees: Russell Todd Nevins, Las Vegas, NV (US); David Jon Backstein, Ontario (CA); Bradley H. Nathan, Ontario (CA)

( * ) Notice: Subject to any disclaimer, the term of this patent is extended or adjusted under 35 U.S.C. 154(b) by 370 days.

(21) Appl. No.: 17/685,345

(22) Filed: Mar. 2, 2022

(65) Prior Publication Data

US 2022/0183705 A1 Jun. 16, 2022

Related U.S. Application Data

(60) Division of application No. 17/486,704, filed on Sep. 27, 2021, now Pat. No. 11,571,225, which is a
(Continued)

(51) Int. Cl.
*A61B 34/10* (2016.01)
*A61B 17/17* (2006.01)
(Continued)

(52) U.S. Cl.
CPC .......... *A61B 17/1764* (2013.01); *A61B 34/20* (2016.02); *A61B 90/39* (2016.02);
(Continued)

(58) Field of Classification Search
CPC .......... A61B 2034/107; A61B 17/17–17/1796
See application file for complete search history.

(56) References Cited

U.S. PATENT DOCUMENTS 7,331,929 B2 2/2008 Morita et al.
7,812,815 B2 10/2010 Banerjee
(Continued)

FOREIGN PATENT DOCUMENTS

CN 107430437 A 12/2017
CN 110430809 A 11/2019
(Continued)

OTHER PUBLICATIONS

Microsoft HoloLens & Mixed /Reality Healthcare Industry Deck, unknown author, at least as early as Oct. 14, 2019.
(Continued)

*Primary Examiner* — Zade Coley
(74) *Attorney, Agent, or Firm* — MORRISS O'BRYANT COMPAGNI CANNON, PLLC

(57) ABSTRACT

A system determining a location for a surgical procedure, the system including a jig having a frame, a first marker fixed to the frame, wherein the first marker includes a scanable label, and a second marker moveably connected to the frame, such that the second marker can move positions independent of the frame, and wherein the second marker includes a scanable label. The system also includes a mixed reality headset configured to scan the scanable label of the first marker and the scanable label of the second marker, to provide location data to the mixed reality headset.

30 Claims, 5 Drawing Sheets

Related U.S. Application Data continuation of application No. 17/373,613, filed on Jul. 12, 2021, now abandoned, which is a continuation of application No. 17/169,289, filed on Feb. 5, 2021, now abandoned, which is a continuation of application No. 17/030,352, filed on Sep. 23, 2020, now abandoned, which is a continuation of application No. 16/994,663, filed on Aug. 17, 2020, now abandoned.

(51) Int. Cl.
*A61B 34/20* (2016.01)
*A61B 90/00* (2016.01)
*G02B 27/01* (2006.01)
*G06F 3/01* (2006.01)

(52) U.S. Cl.
CPC ............ *G02B 27/017* (2013.01); *G06F 3/011* (2013.01); *A61B 2090/395* (2016.02)

(56) References Cited

U.S. PATENT DOCUMENTS

| | | | |
|---|---|---|---|
| 8,123,754 | B2 | 2/2012 | Siebel |
| 8,560,047 | B2 | 10/2013 | Haider et al. |
| 8,876,830 | B2 * | 11/2014 | Hodorek ............ A61B 17/155 606/88 |
| 8,954,181 | B2 | 2/2015 | MacLeod et al. |
| 8,956,165 | B2 | 2/2015 | Kurenov |
| 9,563,266 | B2 | 2/2017 | Banerjee |
| 9,730,713 | B2 | 8/2017 | Park |
| 9,861,446 | B2 * | 1/2018 | Lang ............... A61B 17/1778 |
| 9,892,564 | B1 | 2/2018 | Cvetko et al. |
| 9,978,141 | B2 | 5/2018 | Stolka et al. |
| 9,980,780 | B2 | 5/2018 | Lang |
| 10,016,243 | B2 | 7/2018 | Esterberg |
| 10,108,266 | B2 | 10/2018 | Banerjee |
| 10,159,530 | B2 | 12/2018 | Lang |
| 10,194,990 | B2 * | 2/2019 | Amanatullah ......... A61B 34/20 |
| 10,220,181 | B2 | 3/2019 | Giap |
| 10,241,569 | B2 | 3/2019 | Lanman |
| 10,278,777 | B1 | 5/2019 | Lang |
| 10,285,765 | B2 | 5/2019 | Sachs |
| 10,286,179 | B2 | 5/2019 | Giap |
| 10,292,768 | B2 | 5/2019 | Lang |
| 10,368,947 | B2 | 8/2019 | Lang |
| 10,401,954 | B2 | 9/2019 | Koker |
| 10,405,873 | B2 | 9/2019 | Amiot |
| 10,405,927 | B1 | 9/2019 | Lang |
| 10,437,335 | B2 | 10/2019 | Daniels |
| 10,437,339 | B2 | 10/2019 | Banerjee |
| 10,602,114 | B2 | 3/2020 | Casas |
| 10,672,288 | B2 | 6/2020 | Ribeira et al. |
| 10,716,643 | B2 | 7/2020 | Justin et al. |
| 10,888,399 | B2 | 1/2021 | Kopelman et al. |
| 10,980,601 | B2 | 4/2021 | Yang et al. |
| 11,045,263 | B1 | 6/2021 | Nevins et al. |
| 11,172,990 | B2 | 11/2021 | Lang |
| 2005/0251030 | A1 * | 11/2005 | Azar ............... A61B 90/36 600/429 |
| 2008/0183179 | A1 | 7/2008 | Siebel |
| 2009/0163923 | A1 * | 6/2009 | Flett ............... A61B 17/17 606/89 |
| 2014/0222462 | A1 | 8/2014 | Shakil et al. |
| 2016/0191887 | A1 * | 6/2016 | Casas ............ G06T 19/006 348/47 |
| 2017/0245781 | A1 | 8/2017 | Kay |
| 2017/0258526 | A1 * | 9/2017 | Lang ............... A61B 17/1775 |
| 2017/0312032 | A1 * | 11/2017 | Amanatullah ......... G09B 23/30 |
| 2017/0367766 | A1 | 12/2017 | Mahfouz |
| 2017/0367771 | A1 | 12/2017 | Tako et al. |
| 2018/0049622 | A1 * | 2/2018 | Ryan ............... A61B 1/0005 |
| 2018/0090029 | A1 | 3/2018 | Fisher |
| 2018/0098813 | A1 | 4/2018 | Nesichi |
| 2018/0116728 | A1 | 5/2018 | Lang |
| 2018/0240276 | A1 | 8/2018 | He et al. |
| 2018/0348876 | A1 | 12/2018 | Banerjee |
| 2019/0038362 | A1 | 2/2019 | Nash et al. |
| 2019/0076198 | A1 | 3/2019 | Berend |
| 2019/0110842 | A1 | 4/2019 | Lang |
| 2019/0142520 | A1 | 5/2019 | VanDyken |
| 2019/0149797 | A1 | 5/2019 | Casas |
| 2019/0216562 | A1 | 7/2019 | Sachs |
| 2019/0262078 | A1 | 8/2019 | Lang |
| 2019/0366030 | A1 | 12/2019 | Giap et al. |
| 2019/0380792 | A1 | 12/2019 | Poltaretskyi et al. |
| 2020/0000527 | A1 | 1/2020 | Cazal |
| 2020/0037043 | A1 | 1/2020 | Phillips et al. |
| 2020/0078100 | A1 | 3/2020 | Weinstein et al. |
| 2020/0107003 | A1 | 4/2020 | Phillips et al. |
| 2020/0275976 | A1 * | 9/2020 | McKinnon ............ A61B 90/37 |
| 2020/0275988 | A1 | 9/2020 | Johnson et al. |
| 2020/0302694 | A1 | 9/2020 | Flexman et al. |
| 2020/0360093 | A1 | 11/2020 | Khan et al. |
| 2020/0375666 | A1 * | 12/2020 | Murphy ............... A61B 34/20 |
| 2021/0093329 | A1 | 4/2021 | Poltaretskyi et al. |
| 2021/0093391 | A1 | 4/2021 | Poltaretskyi et al. |
| 2021/0093413 | A1 | 4/2021 | Poltaretskyi et al. |
| 2021/0228286 | A1 | 7/2021 | Moghaddam et al. |
| 2021/0228308 | A1 | 7/2021 | Berger et al. |
| 2021/0244481 | A1 | 8/2021 | Jaramaz et al. |
| 2022/0047279 | A1 | 2/2022 | Nevins et al. |
| 2022/0051483 | A1 | 2/2022 | Nevins et al. |

FOREIGN PATENT DOCUMENTS

| | | |
|---|---|---|
| CN | 110431636 A | 11/2019 |
| DE | 10103922 A1 | 8/2002 |
| DE | 102015212352 A1 | 1/2017 |
| EP | 3113682 B1 | 1/2017 |
| GB | 2570758 A | 7/2019 |
| JP | 2020-515891 A | 5/2020 |
| WO | 2007/108776 A2 | 9/2007 |
| WO | 2012/033739 A2 | 3/2012 |
| WO | 2015/134953 A1 | 9/2015 |
| WO | 2017/066373 A1 | 4/2017 |
| WO | 2018/007091 A1 | 1/2018 |
| WO | 2018132804 A1 | 7/2018 |
| WO | 2018/175971 A1 | 9/2018 |
| WO | 2019051080 A1 | 3/2019 |
| WO | 2019/245870 A1 | 12/2019 |
| WO | 2020033568 A2 | 2/2020 |
| WO | 2020037308 A1 | 2/2020 |
| WO | 2020047051 A1 | 3/2020 |
| WO | 2020145826 A1 | 7/2020 |
| WO | 2021094354 A1 | 5/2021 |

OTHER PUBLICATIONS

Kaluschke et al., HIPS—A Virtual Reality Hip Prosthesis Implantation Simulator, retrieved at https://www.reasearchgate.net/publication/327329265, upload date Sep. 3, 2018 DOI: 10.1109/VR.2018.8446370.

Vaughan et al., Does Virtual-Reality Training on Orthopaedic Simulators Improve Performance in the Operating Room? Science and Information Conference 2015, Jul. 28-30, 2015, London, UK; retrieved at https://www.researchgate.net/publication/284415791; DOI: 10.1109/SAI.2015.7237125.

Patently Apple—Apple Reveals a Mixed Reality Headset that Uses a Direct Retinal Projector System With Holographic Lenses, retrieved at https://www.patentlyapple.com/patently-apple/2019/09/apple-reveals-a-mixed-reality-headset-that-uses-a-direct-retinal-projector-system-with-hologra . . . ; posted date Sep. 19, 2019.

Virtual Reality System Helps Surgeons, Reassures Patients, retrieved at https/medicalgiving.stanford.edu/news/virtual-reality-system-helps-surgeons-reassures-patients.html, retrieved date Oct. 24, 2019.

Immersive Touch Launches the First Virtual Reality Integrated Suite for Surgical Planning, retrieved at https://spinalnewsinternational.com/immersivetouch-virtual-reality-suite, dated Oct. 5, 2018.

(56) References Cited

OTHER PUBLICATIONS

Daley, Sam, The Cutting Edge: 10 Companies Bringing Virtual Reality & AR to the OR, retrieved at https://builtin.com/healthcare-technology/augmented-virtual-reality-surgery, dated Jul. 5, 2019.
Barad, Justin, Virtual and Augmented Reality Can Save Lives by Improving Surgeons' Training, retrieved at https://www.statnews.com/2019/08/16/virtual-reality-improve-surgeon-training, dated Aug. 16, 2019.
Levin et al., The Future of Virtual Reality in Ophthalmology Is Already Here, retrieved at https://www.aao.org/young-ophthalmologists/yo-info/article/future-of-virtual-reality-in-ophthalmology, dated Aug. 16, 2019.
Vaughan et al., A Review of Virtual Reality Based Training Simulators for Orthopaedic Surgery, retrieved at https://www.researchgate.net/publication/283727217, posted date Feb. 22, 2019, DOI: 10.1016/j.medengphy.2015.11.021.
LexInnova Patent Landscape Analysis, Virtual Reality, unknown author, copyright date of 2015.
Virtual & Augmented Reality Are You Sure it Isn't Real? Kathleen Boyle, CFA, Managing Editor, Citi GPS dated Oct. 2016.
New Apple patent filing shows a mixed reality headset that tracks your whole face, Jul. 22, 2019, (downloaded Jul. 1, 2020 at https://www.theverge.com/2019/7/22/20705158/apple-mixed-reality-headset-ar-glasses-patent-application-face-tracking), 2 pages.
"Augmented and virtual reality in surgery-the digital surgical environment: application, limitations and legal pitfalls," accessed at https://www.ncbi.nlm.nih.gov/pmc/articles/PMC5220044/, visited on Jul. 4, 2020. 12 pages.
"The impact of Web3D technologies on medical education and training," Science Direct, accessed at https://www.sciencedirect.com/science/article/pii/S0360131505000825, visited on Jul. 4, 2020, 11 pages.
"Mixed Reality with Hololens: Where Virtual Reality Meets Augmented Reality in the Operating Room," accessed at https://www.ingentaconnect.com/content/wk/prs/2017/00000140/00000005/art00063, visited on Jul. 4, 2020, 1 page.
"Virtual Reality Simulation in Neurosurgery: Technologies and Evolution," Abstract, accessed at https://academic.oup.com/neurosurgery/article-abstract/72/suppl_1/A154/2417686, visited on Jul. 4, 2020, 2 pages.
Katanacho, Manuel, Wladimir De la Cadena, and Sebastian Engel. "Surgical navigation with QR codes: Marker detection and pose estimation of QR code markers for surgical navigation." Current Directions in Biomedical Engineering 2.1 (2016): 355-358.

\* cited by examiner

SYSTEM AND METHOD FOR LOCATION DETERMINATION USING MOVEMENT BETWEEN OPTICAL LABELS AND A 3D SPATIAL MAPPING CAMERA

CROSS-REFERENCE TO RELATED APPLICATIONS

This application is a divisional of non-provisional U.S. patent application Ser. No. 17/486,704, filed on Sep. 27, 2021, which is a continuation of non-provisional U.S. patent application Ser. No. 17/373,613, filed on Jul. 12, 2021, which is a continuation of non-provisional U.S. patent application Ser. No. 17/169,289, filed on Feb. 5, 2021, which is a continuation of non-provisional U.S. patent application Ser. No. 17/030,352, filed on Sep. 23, 2020, which is a continuation of non-provisional U.S. patent application Ser. No. 16/994,663, filed on Aug. 17, 2020, which is hereby incorporated by reference herein in its entirety, including but not limited to those portions that specifically appear hereinafter, the incorporation by reference being made with the following exception: in the event that any portion of the above-referenced application is inconsistent with this application, this application superseded said above-referenced application.

STATEMENT REGARDING FEDERALLY SPONSORED RESEARCH OR DEVELOPMENT

Not applicable.

BACKGROUND

1. The Field of the Present Disclosure

The present disclosure relates generally to surgical systems and methods of facilitating the efficiency and accuracy of implanting surgical prostheses using moveable jig labels, mixed reality and 3D spacial mapping devices.

2. Description of Related Art

In traditional implant surgeries, for example, knee replacements, a surgeon will utilize a metal jig which is used as a drilling or cutting guide to make the necessary corresponding cuts and holes in the bone of the knee to facilitate placement and attachment of the implant to the bone. However, these metal jigs must be stocked in a variety of different sizes to accommodate different needs and sizes of patients, accordingly, significant stocks of metal jigs must be stored and sterilize. Additionally, use of these metal jigs include inherent inaccuracies as the surgeons fix the metal jigs with respect to the corresponding bone during use as a drill or cutting guide.

The femoral implant and tibial implant are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion. In some instances however, it may be necessary to replace or modify an existing femoral and/or tibial implant. Such replacements are generally referred to as revision implants.

To prepare a femur and tibia for such a knee replacement and form an engagement with femoral and tibial implants, the femur and tibia bones must be cut in very specific and precise ways and at very specific and precise angles and locations, so that the prepared bone will properly engage with and be secured to the corresponding implants. In order to make these cuts properly, a surgeon traditionally uses a jig, or surgical cutting guide as known to those skilled in the field, which can be removably attached or secured to the bone, such that slots, or guides, in the jig facilitate the precise cuts necessary to secure the corresponding implants.

The phrase "jig" as used herein, shall thus refer broadly to a surgical cutting guide, that may be configured and arranged to be fixed or attached to a bone, or may be secured adjacent to a bone or other tissue to be cut by a surgeon an identify a relative location, angle and or cutting plane that a surgeon should cut on the adjacent bone or tissue, as known in the art. A jig may include predetermined slots and/or cutting surfaces to identify where a surgeon should cut the adjacent bone or tissue, wherein such cuts may correspond to a shape of a surgical implant that may be attached to the cut bone or tissue. A "cutting surface" may refer to a guide edge for guiding the path of a cutting instrument.

Conventional jigs are typically made of a metal alloy and, due to the precise tolerances at which these jigs must be machined, are quite expensive, ranging as high as $40,000-$50,000 in some cases. These metal jigs must also be stored and reused, which adds additional cost and space resources. Additionally, jigs of various sizes must be kept on had to accommodate patients of different sizes and needs.

Therefore, there is a need for a system that can utilize a less expensive jig, such as a plastic jig, that could be made easily and on demand, while maintaining the required tolerances and enable the same accuracy in use in a surgical procedure.

In other conventional embodiments, holographic jigs, also referred to a virtual jigs, have been used to enable a surgeon to visualize the positioning and proper sizing of a jig to a bone. However, in use, when the surgeon attempts to superimpose a physical jig over the virtual jig to attach it to a bone to make the required bone cuts, the physical jig will impair the view of the virtual or holographic jig, making it difficult to utilize the holographic jig to accurately place the physical jig.

Accordingly, there is a need for a system and method of utilizing a virtual or holographic jig or surgical instrument that could facilitate increased accuracy and precision of required or desired bone cuts.

The phrase "virtual jig" or "holographic jig" as used herein, shall thus refer broadly to any visual rendering or projection representing an actual physical jig, having all, or mostly all, of the same visual characteristics of the physical jig, including size and shape, as known in the art.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. Any discussion of documents, acts, materials, devices, articles or the like which has been included in the present specification is not to be taken as an admission that any or all of these matters form part of the prior art base, or were common general knowledge in the field relevant to the present disclosure as it existed before the priority date of each claim of this application.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
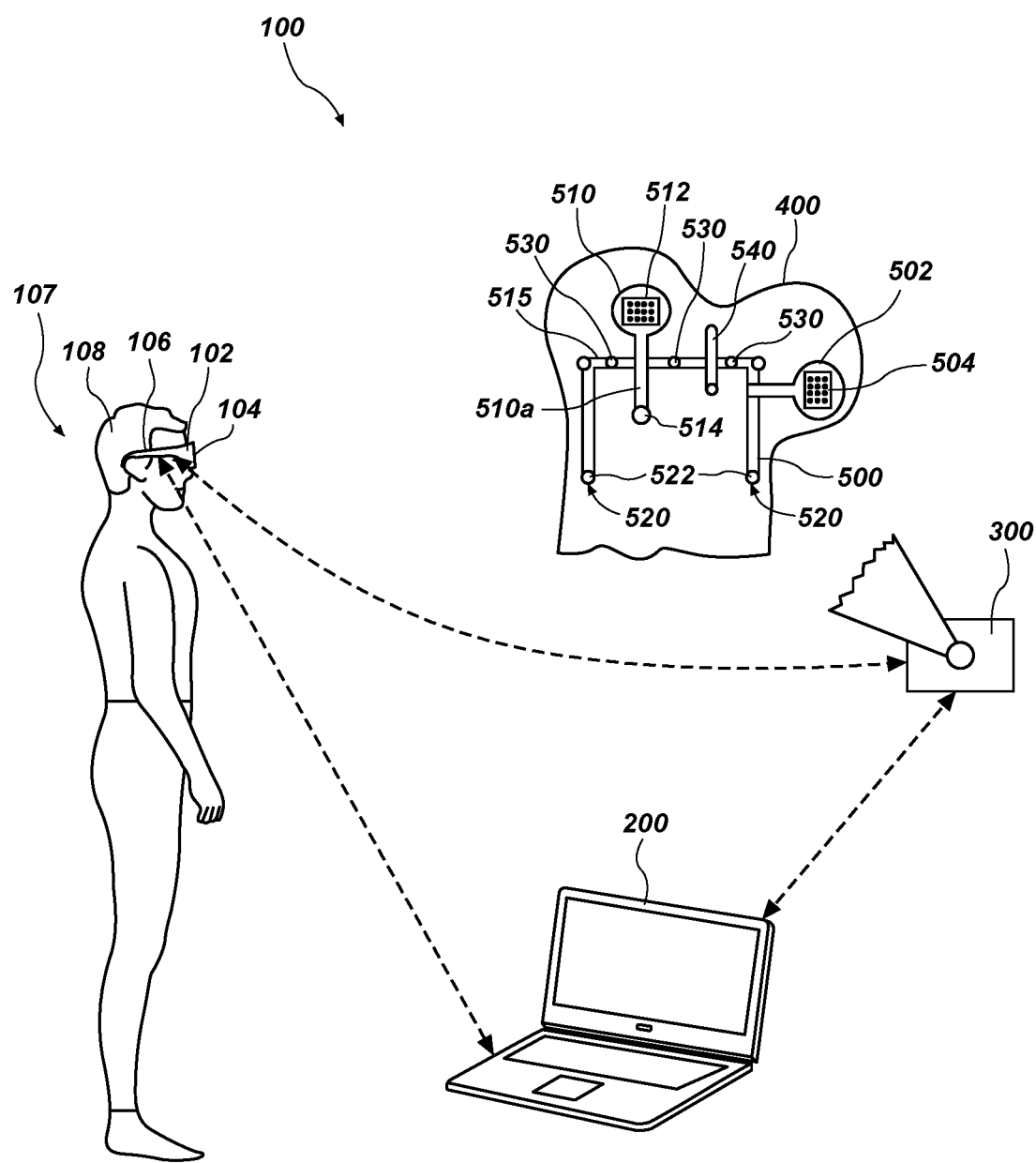
FIG. 1 is a schematic rendering of a mixed reality system of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the terms "virtual," and "hologram" are used interchangeably, and grammatical equivalents thereof are inclusive or open-ended terms that do not exclude additional, unrecited elements or method steps. These terms are used to describe visual representations of an actual physical device or element, having all, or mostly all, of the same visual characteristics of the physical device, including size and shape.

Applicant has discovered a novel system and method for generating and using a virtual jig, or virtual instrument, in a surgical procedure, for example, in a knee or tibial implant procedure, or other desired surgical procedure.

The phrase "virtual system" as used herein, shall refer broadly to any system capable of generating or creating a simulated or virtual rendering or projection of physical or structural features identical or substantially identical to an actual physical device, instrument or other physical structure, as known in the art. A virtual system may also include a device, mechanism, or instrument capable of projecting or displaying the desired a simulated or virtual rendering or projection of physical or structural features identical or substantially identical to an actual physical device. A virtual system may also enable a user to manipulate, move and/or modify the simulated or virtual rendering or projection.

The phrase "mixed or augmented reality system" as used herein, shall refer broadly to any system capable of generating or creating a simulated or virtual rendering or projection of physical or structural features identical or substantially identical to an actual physical device, instrument or other physical structure, as known in the art. A mixed or augmented reality system may also include a device, mechanism, or instrument capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality system may also enable a user to manipulate, move and/or modify the simulated or virtual rendering or projection.

The phrase "mixed or augmented reality instrument" as used herein, shall refer broadly to any device, mechanism or instrument used in a mixed or augmented reality system, including a device capable of generating or creating a simulated or virtual rendering or projection of physical or structural features identical or substantially identical to an actual physical device, instrument or other physical structure, as known in the art. A mixed or augmented reality instrument may also be capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality instrument may also enable a user to manipulate, move and/or modify the simulated or virtual rendering or projection.

The phrase "holographic representation" as used herein, shall refer broadly to a visual rendering or projection representing an actual physical device or element, having all, or mostly all, of the same visual characteristics of the corresponding physical device or element, including size and shape, as known in the art.

Figure 2:
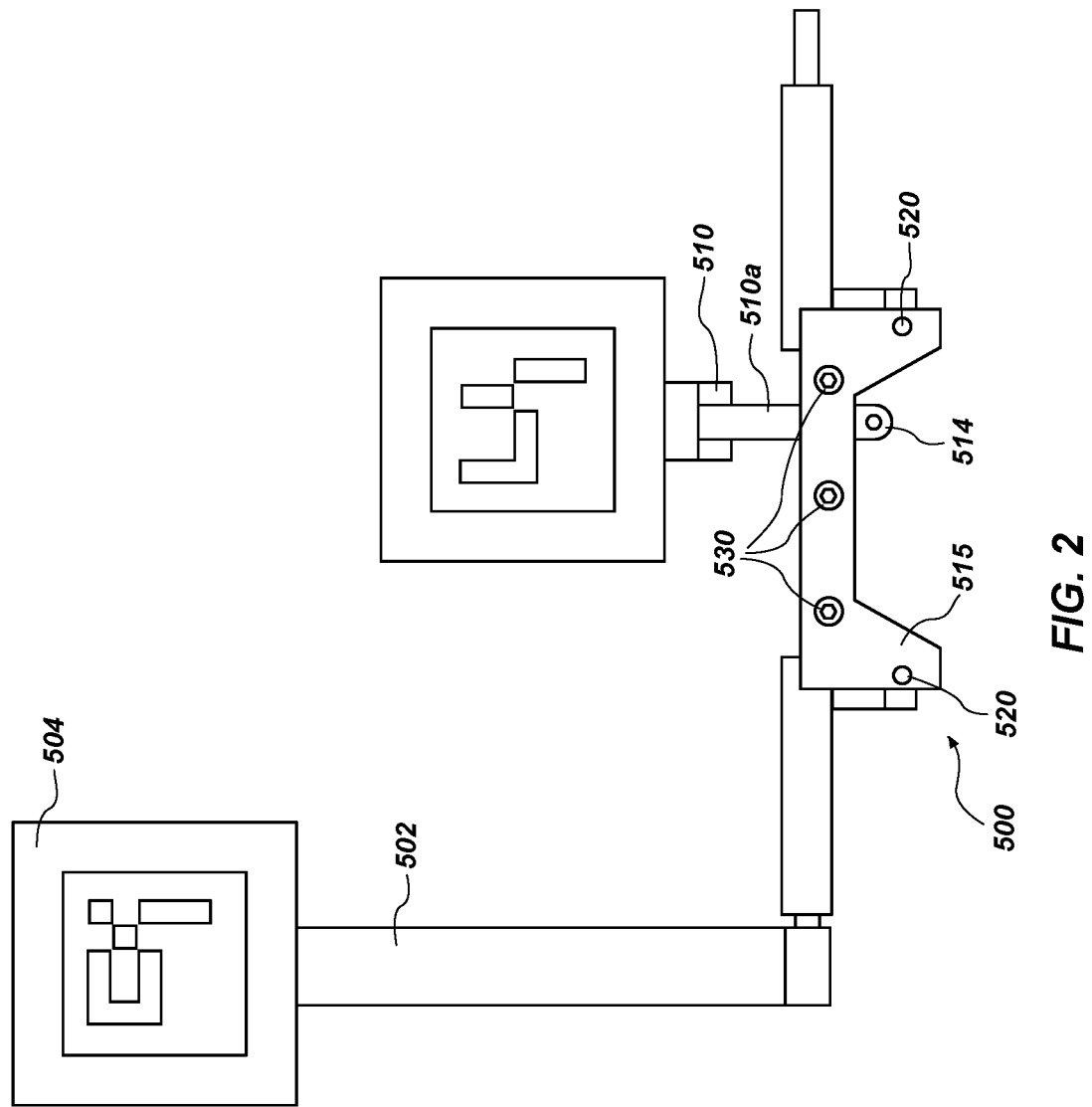
FIG. 2 is a front view of a jig of the present disclosure.
Figure 3:
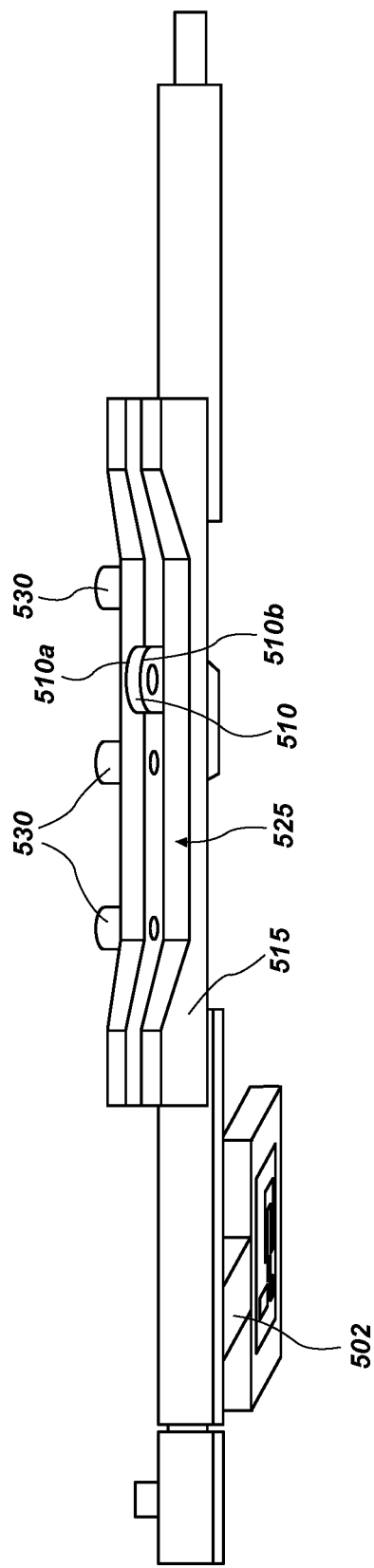
FIG. 3 is a side view of the jig of FIG. 2.

Referring to FIGS. 1-3, in a disclosed embodiment a mixed or augmented system 100, which can be used to produce, or display, a desired mixed or augmented reality instrument, such as a virtual jig or cutting guide in a display to a surgeon or user, or stated another way, that is visible and manipulatable by a surgeon or user. The mixed or augmented reality system 100 may also enable a user to activate or deactivate, in full or in part, the virtual instrument or instruments, making a virtual instrument appear or disappear, as desired in a mixed reality assisted surgery, for example.

The mixed or augmented reality system 100 may include a mixed or augmented reality headset 102 which may include a transparent or mostly transparent viewer 104 which can be suspended or positioned in front of a user's eyes. The headset 102 may include a headband 106 attached to the viewer 104, which may be used to secure the headset 102 to a user's head 108, thereby securing the viewer 104 in place in front of the user's eyes.

The transparent viewer 104 may be configured to project, or otherwise make viewable, on an interior surface of the viewer 104, a holographic image or images, such as a virtual device, for example, a virtual cutting guide, which may be positionally manipulated by the user, surgeon, third party or remote system, such as a remote computer system. The headset 102 may be configured to view holographic images or, alternatively, the holographic images may be turned off and the user wearing the headset 102 may be able to view the surrounding environment through the transparent viewer 104, unobstructed. As such, a user, such as a surgeon for example, can wear the mixed or augmented reality headset 102 and then can choose to activate a holographic image to aide in facilitating a surgical procedure and then shut off the holographic image in order to perform the surgical procedure un-obscured, visually.

One embodiment of the disclosed headset 102 may be a product created and manufactured by Microsoft, known as the HoloLens® mixed or augmented reality system, or any suitable mixed or augmented reality system for generating virtual images viewable by a user or surgeon. Headset 102 may be a conventional "off the shelf" product with a built-in platform that enables all of the features described herein with respect to the headset 102. Furthermore, the headset 102, such as a Microsoft HoloLens product, can be loaded or preloaded with all desired or required virtual instruments, including virtual jigs or surgical cutting guides, virtual drill bits, and/or a virtual target which can identify relative locations of a plurality of holes to be drilled by a surgeon to facilitate the fastening of a jig or other device onto a desired bone at the proper desired location, and any other desired virtual instruments or holograms. The Microsoft HoloLens product and its capabilities and features, or any suitable mixed or augmented reality system such as is described herein with respect to the headset 102, are known to those skilled in the art.

The mixed reality system 100 may also include a computer or computer system 200 having enabling software to communicate with the headset 102, by both receiving information from the headset 102 and transmitting data and images to the headset 102. It is therefore to be understood, by way of the circuit diagram and dashed lines shown in FIG. 1, that headset 102 is electronically connected to the computer system 200 and a 3D spatial mapping camera 300. The 3D spatial mapping camera 300 is electronically connected to the headset 102 and the computer system 200, as shown in the circuit diagram and dashed lines shown in FIG. 1. While the 3D spatial mapping camera 300 is electronically connected to the headset 102, the 3D spatial mapping camera 300 may be separate from and not mechanically connected to the headset 102.

The mixed reality system 100 may also include a 3D spatial mapping camera 300. One embodiment of the disclosed spatial mapping camera 300 may be a product created and manufactured by Microsoft, known as the Azure Kinect®, or any suitable 3D spatial mapping camera capable of continuous 3D mapping and transition corresponding 3D images, such as bones, anatomy, or other desired 3D objects. The spatial mapping camera 300 may be a conventional "off the shelf" product with a built-in platform that enables all of the features described herein with respect to the spatial mapping camera 200. Furthermore, the spatial mapping camera 200, such as a Microsoft Azure Kinect product, can be loaded or preloaded with all necessary software to enable wireless communication between the spatial mapping camera 300 and the computer system 200 and/or the headset 102. The Microsoft Azure Kinect product and its capabilities and features, or any suitable 3D spatial mapping camera such as is described herein with respect to the spatial mapping camera 300, are known to those skilled in the art.

The headset 102, computer system 200 and spatial mapping camera 300, may be programmed and configured to enable a surgeon 107 to see and manipulate a virtual, or holographic target or jig, with respect a patient's bone 400, anatomical, or any other desired location, which may receive a surgical implant. The headset 102, computer system 200 and spatial mapping camera 300 may communicate with one another via a local network connection, wifi, bluetooth, or any other known wireless communication signal.

Specifically, the spatial mapping camera 300, that may be programmed to communicate with the computer system 200 having enabling software, may utilize such enabling software to map the bone 400, or other desired anatomy, to help identify the proper location for fastening a jig, or other device, to the bone 400, prior to cutting the knee.

The mixed reality system 100 may also include an alignment jig 500 that can be secured to the exposed bone 400, or other desired anatomy. The jig 500 may includes a first marker 502 which may be attached to the jig 500 at a fixed location on the bone 400. The first marker 502 may include a scanable, visual, optical label 404, such as a QR code. The jig 500 may also include a second marker 510 that may be moveable with respect to the jig 500 and the bone 400. The second marker 510 may also include a scanable, visual, or optical label 412, such as a QR code.

The surgeon may attach the jig 500 to the exposed bone 400, at a predetermined or desired location. The spatial mapping camera 300 may spatially map the jig 500 and the exposed bone 400, to map the surface of the exposed bone and relative location of the jig 500.

The surgeon may then utilize the headset 102 to scan the fixed scanable label 504 of the first marker 502 and send the corresponding information to the computer system 200. The computer system 200 may then utilize data from the 3D spatial mapping camera 300 and the scanable label 502 of the first marker 502 to determine the orientation of the moveable second marker 510 and send the data to the headset 100, which can then utilize the data provided by the scanable label 512 to determine the substantially exact proper location of the second marker 510. This identified position of the second marker 510 may be viewed by the surgeon in a holographic image. The surgeon can then manipulate the second marker 510 in the holographic image, until the proper position is set and determined.

Once the proper position of the second marker 510 is set in the holographic image the surgeon can use the headset 102 to lock the holographic image in place. Then the surgeon can manipulate the actual physical second marker 510 to substantially match the positioning of the set rendering of the second marker 510. A target 514 located on the second marker 510 may provide the surgeon with the substantially exact location to drill a required hole, or place a pin, with respect to the exposed bone 400, such that the surgeon can manipulate the location of the jig with respect to the bone 400, to substantially match the location of the virtual jig, or holographic image 900, with respect to a virtual bone.

The headset 102 may help facilitate the proper orientation of the second marker 510, and corresponding target 514, by illuminating the target 514 or providing a colored symbol, each of which may include a color, such as red, that may change colors, such as changing from red to green, when the target is ultimately moved into the proper position, by operation of a microprocessor (not shown) contained within headset 102 or computer system 200, said processor being programmed as known to those skilled in the art of programming to trigger a change of color when the target is moved into the proper position.

As shown in FIGS. 2-5 the jig 500 may include a frame 515 that may be generally U-shaped, although alternative shapes may also be used, such as a V-shape, semi-circle, or any other desired shape, for example. A partially enclosed, or open-ended shape may provide a surgeon or user with the ability to manipulate the position of the second marker 510 over a broader range of motion.

The jig 500 may include a plurality of pin holes 520, in the frame 515, which can be configured to receive corresponding pins 522 which can removably attach the jig 500 to the bone 400.

The frame 515 of the jig 500 may also include slot 525 that extends through at least a portion of the frame 515. The slot may also lie in substantially the same plane as the frame 515 or substantially parallel to the plane of the frame 515. The slot 525 may be configured to receive at least a portion of the second marker 510.

The second marker 510 may be formed having a substantially rectangular cross-section, such that the second marker 515 includes at least a pair of opposing, substantially planar side surfaces 510a and 510b. The second marker 510 may also be formed in a generally linear shape, as shown, but may alternatively be bent, angled, or have any other desired shape.

The slot 525 of the frame 515 may be shaped and configured to receive the second marker 510 in a friction fit relationship, such that the second marker 510 can be inserted into the slot 525 of the frame 515 and positionally manipulated, laterally, horizontally or in any desired direction, with respect to the frame 515. The slot 515 enables the second marker 510 to move translationally 360 degrees, with respect to the frame 515, within a single plane, where such a plane is substantially coplanar with a plane formed by the slot 525.

Once the second marker 510 is located in a desired position within the slot 525 with respect to the frame 515, locking pins 530 may be threaded through the frame 515 and slot 525 and fastened, such that a portion of the frame 515 adjacent to the portion of the second marker 510 within the slot 525 is biased against the second marker 510, locking the second marker 510 in place, relative to the frame 515 and slot 525. While the locking pins 530, may be in a threaded relationship with the fame 515, other mocking mechanisms know in the art may alternatively be used.

The jig 500 may also include a third marker 540 that may be identical, or substantially identical, to the structure of the second marker 510, and may be used in the same or substantially the same way in the mixed reality system as the second marker.

The first, second, and third markers 502, 510, and 540 may be configured such that scanable labels, such as 504 and 512 may be removably secured thereto. These scanable labels 504 and 512, or other similar labels, may be removably secured to respective markers 502, 510 and 540 via friction fit, snap fit, or any other desired securement method. This removable connection enables a surgeon or user to interchange labels between markers or replace or otherwise change labels before, during or after a procedure.

Figure 4:
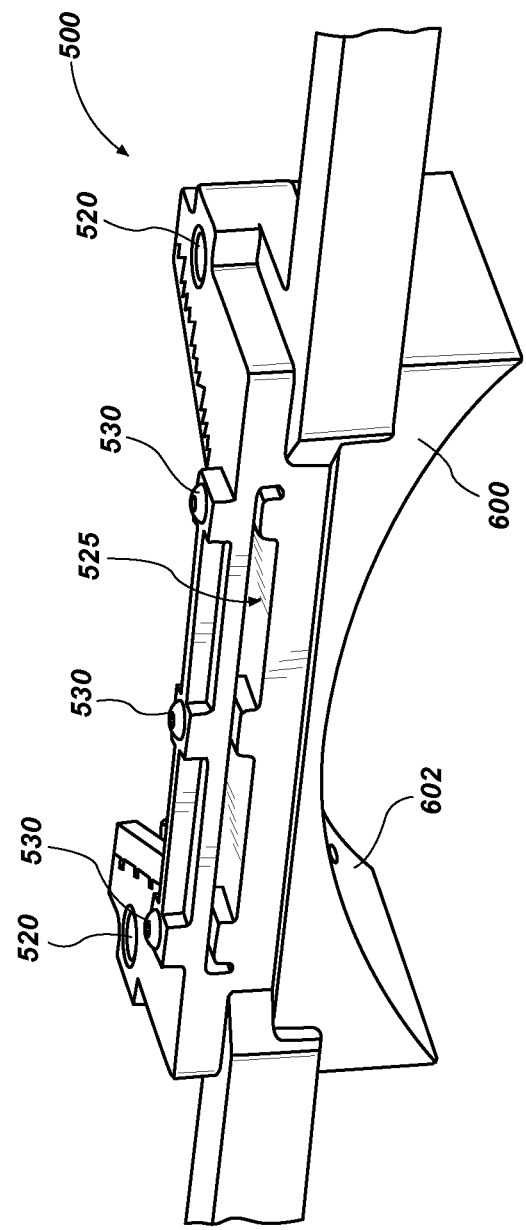
FIG. 4 is a perspective view of a jig and mounting plate of the present disclosure.
Figure 5:
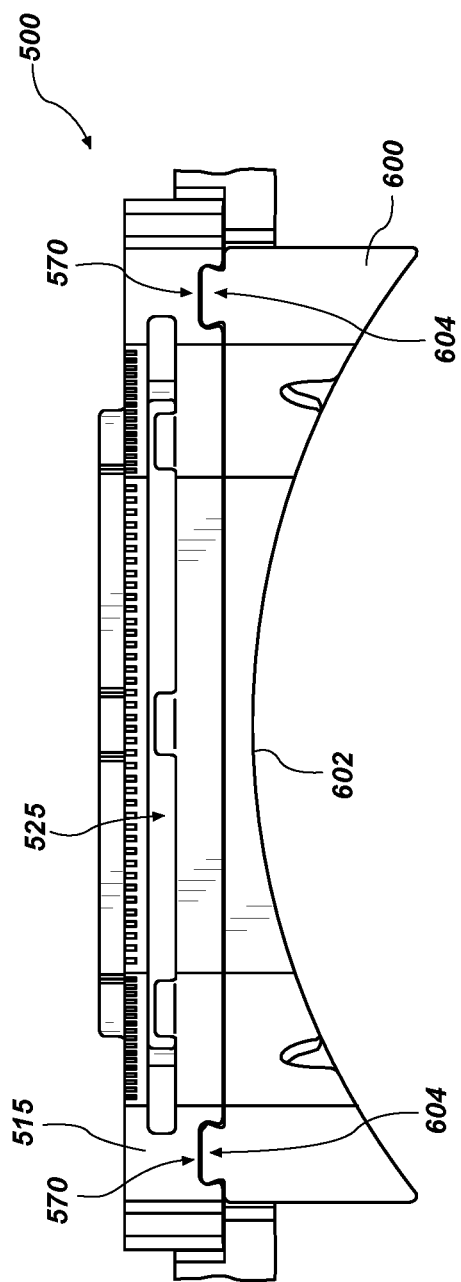
FIG. 5 is a side view the jig and mounting plate of FIG. 4.

As shown in FIGS. 4 and 5, in another embodiment the jig 500 may be removably secured to a mounting plate 600. The mounting plate 600 may include a concave or curved surface 602 that may be shaped and/or configured to abut or receive a portion of a bone, portion of anatomy, or another desired object. The mounting plate may include a pair of key features 604, that may be configured to be received in corresponding key ways 570 formed in the frame 515. The key 604 and key way 570 engagement enables the jig 500 to be removably engaged with the mounting plate 600, such that the jig 500 may be secured to the mounting plate 600 before a surgical procedure has begun, or after the mounting plate 600 has already been positioned with respect to a bone, portion of anatomy, or another desired object.

Due to the accuracy of the disclosed method and system, the jig 500 may be made of plastic, metal, polyamide, or any other desired material. Manufacturing the jig 500 out of a plastic or polyamide material, or other relatively inexpensive material, may allow the jig 500 to be disposable, while still maintaining the precision and accuracy of traditional metal jigs. The jig 500 may also be manufactured using a 3D printer, which can further reduce the cost of manufacturing and storage of jigs, since 3D printed jigs could be made on demand, customized to the size and shape required by individual patients and users. The physical jig 500 may also be manufactured using any other known technique for forming a physical jig.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A method of determining a location for a surgical procedure, comprising:
    attaching a jig to a bone, wherein the jig includes:
        a frame;
        a first marker fixed to the frame, wherein the first marker includes a scanable label;
        a second marker moveably connected to the frame, such that the second marker can move positions independent of the frame, and wherein the second marker includes a scanable label;
        wherein the frame includes a slot configured to receive the second marker;
        at least one locking pin configured to bias the frame against the second marker within the slot;
    providing a 3D spatial mapping camera;
    spatially mapping the jig and the bone using the 3D spatially mapping camera to identify a location for the surgical procedure;
    scanning the scanable label of the first marker and the scanable label of the second marker to identify a location for the second marker; and
    manipulate a position of the second marker to the identified location.

2. The method of claim 1, further comprising:
    providing a mixed reality headset configured to scan the scanable label of the first marker and the scanable label of the second marker, to provide location data to the mixed reality headset.

3. The method of claim 1, wherein the first marker is fixed to the frame such that the first marker does not move independent of the frame.

4. The method of claim 1, wherein the scanable label of the first marker includes data receivable by the mixed reality headset related to the jig.

5. The method of claim 1, wherein the scanable label of the second marker includes data receivable by the mixed reality headset related to a determined position of the second marker.

6. The method of claim 1, wherein the second marker includes a target, configured to identify a location to drill.

7. The method of claim 1, wherein the second marker may move laterally, with respect to the frame, within the slot.

8. The method of claim 7, wherein the slot is configured to receive the second marker with a friction fit engagement.

9. The method of claim 1, further comprising a mounting plate fastened to the frame and configured to abut a bone.

10. The method of claim 1, wherein the scanable label of the first marker is removable.

11. The method of claim 1, wherein the scanable label of the second marker is removable.

12. A method of determining a location for a surgical procedure, comprising:
 attaching a jig to a bone, wherein the jig includes:
  a frame;
  a first marker fixed to the frame, wherein the first marker includes a scanable label;
  a second marker moveably connected to the frame, such that the second marker can move positions independent of the frame, and wherein the second marker includes a scanable label;
  wherein the frame includes a slot configured to receive the second marker;
  at least one locking pin, separate from the second marker, configured to bias the frame against the second marker within the slot;
 providing a 3D spatial mapping camera;
 providing a mixed reality headset configured to communicate with the 3D mapping camera;
 spatially mapping the jig and the bone using the 3D spatially mapping camera to identify a location for the surgical procedure;
 sending a determined location of the second marker from the 3D spatial mapping camera to the mixed reality headset, such that the mixed reality headset provides an image of the determined location for the second marker relative to the bone; and
 manipulating a position of the second marker to the identified location.

13. The method of claim 12, further comprising:
 scanning the scanable label of the first marker and the scanable label of the second marker to identify the determined location for the second marker.

14. The method of claim 12, wherein the first marker is fixed to the frame such that the first marker does not move independent of the frame.

15. The method of claim 12, wherein the scanable label of the first marker includes data receivable by the mixed reality headset related to the jig.

16. The method of claim 12, wherein the scanable label of the second marker includes data receivable by the mixed reality headset related to a determined position of the second marker.

17. The method of claim 12, wherein the second marker includes a target, configured to identify a location to drill.

18. The method of claim 12, wherein the second marker may move laterally, with respect to the frame, within the slot.

19. The method of claim 18, wherein the slot is configured to receive the second marker with a friction fit engagement.

20. The method of claim 12, further comprising a mounting plate fastened to the frame and configured to abut a bone.

21. A method of determining a location for a surgical procedure, comprising:
 attaching a jig to a bone, wherein the jig includes:
  a frame;
  a first marker fixed to the frame, wherein the first marker includes a scanable label;
  a second marker moveably connected to the frame, such that the second marker can move positions independent of the frame, and wherein the second marker includes a scanable label;
  wherein the frame includes a slot configured to receive the second marker, the slot being defined by opposing interior surfaces;
  at least one locking pin configured to bias said opposing interior surfaces of the slot against the second marker;
 providing a mixed reality headset;
 scanning the scanable label of the first marker and the scanable label of the second marker with the mixed reality headset to identify a location for the second marker using the mixed reality headset; and
 manipulating a position of the second marker to the identified location.

22. The method of claim 21, further comprising:
 providing a 3D spatial mapping camera; and
 spatially mapping the jig and the bone using the 3D spatially mapping camera to identify a location for the surgical procedure.

23. The method of claim 21, wherein the first marker is fixed to the frame such that the first marker does not move independent of the frame.

24. The method of claim 21, wherein the scanable label of the first marker includes data receivable by the mixed reality headset related to the jig.

25. The method of claim 21, wherein the scanable label of the second marker includes data receivable by the mixed reality headset related to a determined position of the second marker.

26. The method of claim 21, wherein the second marker includes a target, configured to identify a location to drill.

27. The method of claim 21, wherein the second marker may move laterally, with respect to the frame, within the slot.

28. The method of claim 27, wherein the slot is configured to receive the second marker with a friction fit engagement.

29. The method of claim 21, further comprising a mounting plate fastened to the frame and configured to abut a bone.

30. A method of determining a location for a surgical procedure, comprising:
 providing a 3D spatial mapping camera;
 providing a mixed reality headset;
 attaching a jig to a bone, wherein the jig includes:
  a frame;
  a first marker fixed to the frame, wherein the first marker includes a removable scanable label, wherein the first marker is fixed to the frame such that the first marker does not move independent of the frame and the scanable label of the first marker includes data receivable by the mixed reality headset related to the jig;

a second marker moveably connected to the frame, such that the second marker can move positions independent of the frame, and wherein the second marker includes a removable scanable label that includes data receivable by the mixed reality headset related to a determined position of the second marker and wherein the second marker also includes a target, configured to identify a location to drill;

wherein the frame includes a slot configured to receive the second marker, the slot being defined by opposing interior surfaces, said opposing interior surfaces being disposed in friction fit engagement with the second marker;

at least one locking pin configured to bias said opposing interior surfaces of the slot against the second marker a mounting plate fastened to the frame and configured to abut a bone;

wherein the frame includes a slot configured to receive the second marker, wherein the second marker may move laterally, with respect to the frame, within the slot and wherein the slot is configured to receive the second marker and the slot being defined by opposing interior surfaces, said opposing interior surfaces being disposed in friction fit engagement with the second marker;

at least one locking pin configured to bias said opposing interior surfaces of the slot against the second marker spatially mapping the jig and the bone using the 3D spatially mapping camera to identify a location for the surgical procedure;

scanning the scanable label of the first marker and the scanable label of the second marker with the mixed reality headset to identify a location for the second marker using the mixed reality headset; and manipulating a position of the second marker to the identified location.

\* \* \* \* \*